US008890069B2

(12) United States Patent
Sun et al.

(10) Patent No.: US 8,890,069 B2
(45) Date of Patent: Nov. 18, 2014

(54) METHOD FOR DETECTING DEFECT OF SUBSTRATE

(71) Applicant: Samsung Electronics Co., Ltd., Suwon-si (KR)

(72) Inventors: Jong-Cheon Sun, Seoul (KR);
Hyung-Seop Kim, Seoul (KR);
Hee-Won Sunwoo, Seoul (KR);
Byoung-Ho Lee, Yongin-si (KR);
Dong-Chul Ihm, Suwon-si (KR);
Soo-Bok Chin, Seoul (KR)

(73) Assignee: Samsung Electronics Co., Ltd. (KR)

( * ) Notice: Subject to any disclaimer, the term of this patent is extended or adjusted under 35 U.S.C. 154(b) by 0 days.

(21) Appl. No.: 14/230,506

(22) Filed: Mar. 31, 2014

(65) Prior Publication Data

US 2014/0306109 A1 Oct. 16, 2014

(30) Foreign Application Priority Data

Apr. 12, 2013 (KR) .......................... 10-2013-0040590

(51) Int. Cl.
*H01J 37/153* (2006.01)
*G01N 23/203* (2006.01)
*G01N 23/225* (2006.01)
*H01J 37/26* (2006.01)

(52) U.S. Cl.
CPC ............ *G01N 23/2251* (2013.01); *H01J 37/26* (2013.01)
USPC ........ 250/310; 250/306; 250/307; 250/492.2; 250/492.22; 250/492.3; 250/311; 250/396 R

(58) Field of Classification Search
CPC .............. G01N 23/225; G01N 23/203; G01N 23/2251; H01J 2237/2817; H01J 2237/082; H01J 2237/2806
USPC ................. 250/310, 306, 307, 492.22, 492.2, 250/492.3
See application file for complete search history.

(56) References Cited

U.S. PATENT DOCUMENTS

| | | | | |
|---|---|---|---|---|
| 7,116,816 B2 * | 10/2006 | Tanaka et al. | ................. | 382/149 |
| 7,368,713 B2 * | 5/2008 | Matsui | .......................... | 250/310 |
| 8,289,508 B2 * | 10/2012 | Lim et al. | ................... | 356/237.5 |
| 2001/0033683 A1 | 10/2001 | Tanaka et al. | | |
| 2006/0043292 A1 | 3/2006 | Matsui | | |
| 2008/0176345 A1 * | 7/2008 | Yu et al. | .......................... | 438/17 |
| 2011/0116085 A1 | 5/2011 | Lim et al. | | |

FOREIGN PATENT DOCUMENTS

KR 10-2012-0120823 A 11/2012

* cited by examiner

*Primary Examiner* — Nikita Wells
(74) *Attorney, Agent, or Firm* — Onello & Mello LLP

(57) ABSTRACT

A method for detecting defects includes irradiating at least one electron beam into a first region of a substrate, irradiating at least one electron beam into a second region electrically connected to the first region, and detecting secondary electrons emitted from the second region. The electron beam irradiated into the first region may be the same or different from the electron beam irradiated into the second region. Alternatively, different beams may be simultaneously irradiated into the first and second regions. An image generated based on the secondary electrons shows a defect in the substrate as a region having a grayscale difference with other regions in the image.

19 Claims, 11 Drawing Sheets

METHOD FOR DETECTING DEFECT OF SUBSTRATE

CROSS-REFERENCE TO RELATED APPLICATION

Korean Patent Application No. 10-2013-0040590, filed on Apr. 12, 2013, and entitled, "Method For Detecting Defect Of Substrate," is incorporated by reference herein in its entirety.

BACKGROUND

1. Field

One or more embodiments described herein relate to inspecting substrates.

2. Description of the Related Art

A semiconductor device may be manufactured using a fabrication process (FAB) for forming electrical circuits on a substrate. An electrical die sorting (EDS) process may then be used for testing electrical characteristics of the device. A package assembling process encapsulates the device with an epoxy resin.

Various unit processes may be used for the FAB process. These unit processes include: a deposition process for forming a thin layer on the substrate, a chemical mechanical polishing (CMP) process for polishing the thin layer for planarization, a photolithography process for forming a photoresist pattern on the thin layer, an etching process for forming the thin layer into a pattern having electrical characteristics using the photoresist pattern, an ion implantation process for implanting ions into regions of the substrate, a cleaning process for cleaning impurities from the substrate, and an inspection process for inspecting defects in the thin layer or patterns on the surface of the substrate.

The inspection process may be performed because defects have been shown to degrade operating characteristics of the semiconductor device. Defects may also reduce the production efficiency, and thereby limit the competitiveness of the manufacturing company. Examples of defects include scratches, particles, and unremoved portions of material layers formed on the surface of the semiconductor substrate.

Defects which are not detected during inspection may cause the semiconductor device to malfunction or be inoperative. Examples of devices used to inspect semiconductor devices include electron microscopes (SEMs), transmission electron microscopes (TEMs), and secondary ion mass spectrometry (SIMS) devices which use ion beams. Other devices include surface test devices which use laser beams for inspection.

These and other inspection devices have proven inadequate in a number of ways. For example, these devices demonstrate poor signal-to-noise ratio which limits detection performance. Other devices have other performance defects which cause defects to go undetected.

SUMMARY

In accordance with one embodiment, a method for detecting defects includes irradiating an electron beam into a first region of a substrate; irradiating an electron beam into a second region electrically connected to the first region; and detecting secondary electrons emitted from the second region.

The first region may be a peripheral region and the second region may be a cell region of the substrate. The first region and the second region may be adjacent or separated from each other.

The method may further include generating an image indicating a defect of the substrate. The image may be generated based on a detected amount of secondary electrons. The defect may be detected as corresponding to a location in the image that has a grayscale value different from an adjacent location in the image.

Irradiating the electron beam into the first region may include vertically irradiating the electron beam into a surface of the first region, and irradiating the electron beam into the second region may include vertically irradiating the electron beam into a surface of the second region.

The first region may include a gate region and the second region includes a drain region. The electron beam irradiated into the first region may be the same electron beam irradiated into the second region.

In accordance with another embodiment, a method for detecting defects includes simultaneously irradiating electron beams into a first region of a substrate and a second region electrically connected to the first region; and detecting secondary electrons emitted from the second region. Simultaneously irradiating the electron beams into the first and second regions may include simultaneously irradiating a first electron beam toward the first region and a second electron beam toward the second region.

The first electron beam may be vertically irradiated into a surface of the first region, and the second electron beam may be vertically irradiated into a surface of the second region. The first region and the second region may be adjacent or separated from each other.

The method may further include generating an image indicating a defect of the substrate. Generating the image may include generating the image based on a detected amount of secondary electrons. The defect may be detected as corresponding to a location in the image that has a grayscale value different from an adjacent location in the image.

In accordance with another embodiment, a method for detecting defects includes scanning an electron beam from a first region to a second region of a substrate, the second region corresponding to an inspection region; detecting secondary electrons emitted from the second region; and detecting a defect in the second region of the substrate based on the secondary electrons emitted from the second region, wherein the first region is electrically connected to the second region.

The method may further include generating an image based on the secondary electrons, wherein the image includes a first location and a second location, and wherein the first location has a first grayscale value that exceeds a reference value and the second location has a second gray scale value less than the reference value, the second location detected as corresponding to the defect.

Generating the image may include generating the image based on a detected amount of the secondary electrons. The second grayscale value may be darker than the first grayscale value.

BRIEF DESCRIPTION OF THE DRAWINGS

Features will become apparent to those of ordinary skill in the art by describing in detail exemplary embodiments with reference to the attached drawings in which.

DETAILED DESCRIPTION

Figure 1:
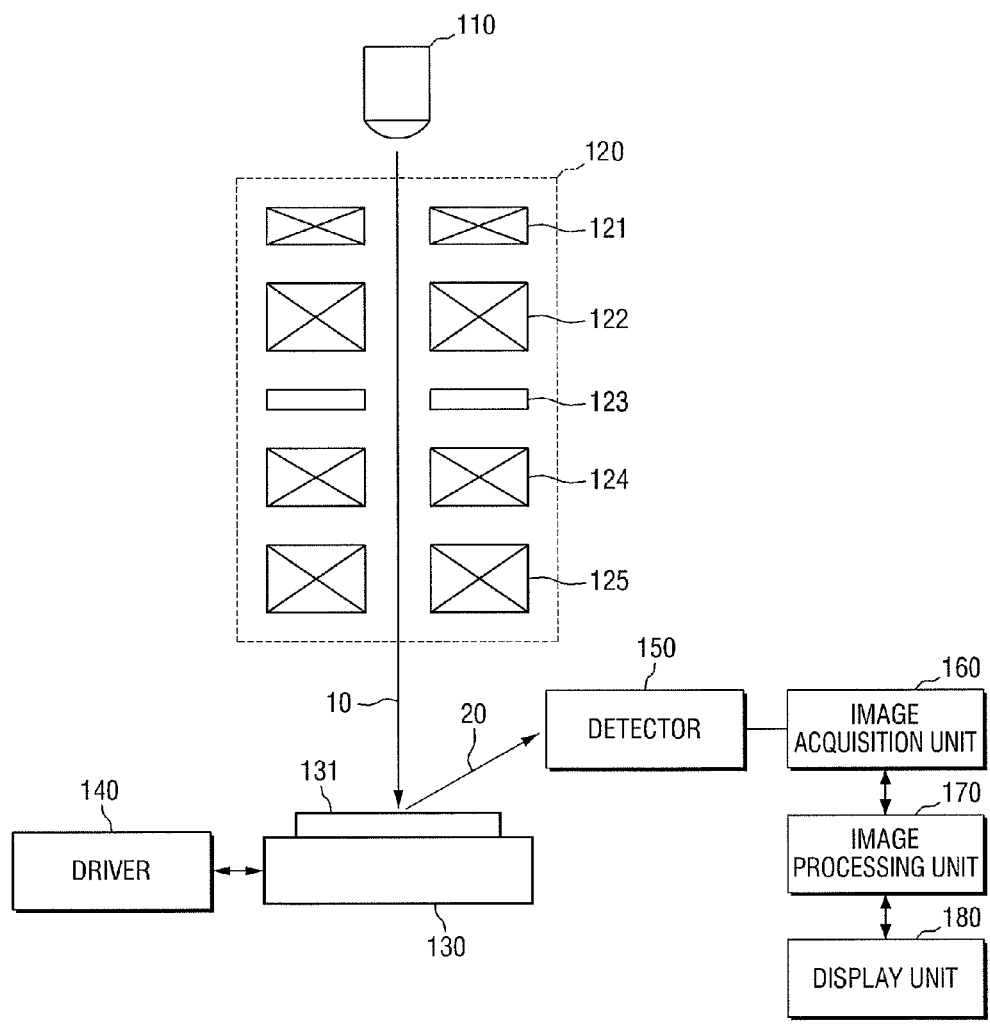
FIG. 1 illustrates an apparatus to detect a substrate defect using electron beams.

Example embodiments are described more fully hereinafter with reference to the accompanying drawings; however, they may be embodied in different forms and should not be construed as limited to the embodiments set forth herein. Rather, these embodiments are provided so that this disclosure will be thorough and complete, and will fully convey exemplary implementations to those skilled in the art.

In the drawing figures, the dimensions of layers and regions may be exaggerated for clarity of illustration. It will also be understood that when a layer or element is referred to as being "on" another layer or substrate, it can be directly on the other layer or substrate, or intervening layers may also be present. Further, it will be understood that when a layer is referred to as being "under" another layer, it can be directly under, and one or more intervening layers may also be present. In addition, it will also be understood that when a layer is referred to as being "between" two layers, it can be the only layer between the two layers, or one or more intervening layers may also be present. Like reference numerals refer to like elements throughout.

FIG. 1 illustrates an apparatus for detecting a defect of a substrate using electron beams. Referring to FIG. 1, the apparatus includes an electron beam source 110 and a column 120. The column 120 includes an axis adjusting coil 121, a focusing lens 122, an iris 123, a scanning coil 124, and an objective lens 125. The apparatus also includes a stage 130 for supporting a substrate 131, a driver 140, a detector 150, an image acquisition unit 160, an image processing unit 170, and a display unit 180.

The electron beam source 110 generates electrons using an electron gun to form electron beams 10. The electron gun may include a filament for generating electrons and an extracting electrode for extracting the electrons.

The column 120 may include a housing for irradiating electron beams 10 toward and into and/or onto a surface of substrate 131. While column 120 is shown to include axis adjusting coil 121, focusing lens 122, iris 123, scanning coil 124, and objective lens 125, one or more of these elements may exist outside of the housing in alternative embodiments.

The axis adjusting coil 121 may be positioned between the electron beam source 110 and the focusing lens 122, and may cause the electron beams 10 to coincide with a central (or other predetermined) axis of the focusing lens 122.

The focusing lens 122 and objective lens 125 may be electromagnets having coils wound thereon to form a magnetic field for focusing electrons. For example, the electron beam 10 may have a cross-sectional area of 10 to 50 μm, and the electron beam irradiated into substrate 131 may have a spot size of approximately 5 to 200 nm. The focusing lens 122 may focus and adjust the intensity of the electron beams 10.

The objective lens 125 may adjust the spot size and focal distance of the electron beam 10, as it is irradiated into the surface of substrate 131. The objective lens 125 may also determine the resolution capability of the substrate defect detecting apparatus. In the case where a distance between the objective lens 125 and substrate 131 is considered a working distance, the spot size of electron beam 10 may be reduced and the resolution of the image may be increased as the working distance is reduced.

The iris 123 may be positioned between the focusing lens 122 and scanning coil 124. The iris 123 may have a light transmitting portion with a predetermined diameter, and may adjust the intensity of the electron beams 10 with the focusing lens 122.

The scanning coil 124 may be positioned between the iris 123 and objective lens 125. The scanning coil 124 may deflect the electron beam 10, to allow the electron beams 10 to scan substrate 131. If the amplitude of current applied to the scanning coil 124 is changed, a magnifying power of the substrate defect detecting apparatus may be freely adjusted.

The stage 130 supports the substrate 131 and is connected to the driver 140. The driver 140 adjusts a position of stage 130 to allow the electron beams 10 to be irradiated into a predetermined region of or the entire surface of substrate 131. For example, the driver 140 may be a robot moving on one plane along rectangular coordinates.

Although not shown in FIG. 1, an additional driver for adjusting a height of the stage 130 may be provided under the stage 130. For example, the additional driver may include a piezoelectric device. If the electron beam 10 is irradiated, secondary electrons 20 and reflected electrons, X rays, backscattered electrons, etc. may be generated from the surface of substrate 131, signals of electrons absorbed into substrate 131, or electrons transmitting through the substrate 131 may also be generated.

The detector 150 may detect secondary electrons 20 emitted from substrate 131 based on electron beam 10, may convert a current signal corresponding to the detected secondary electrons 20 into a voltage signal, and may amplify the voltage signal. A bias voltage for detecting secondary electrons 20 may be applied to detector 150. More specifically, secondary electrons 20 may be emitted from substrate 131 at various angles.

In addition, detector 150 may be positively charged to collect secondary electrons 20 therein. For example, a voltage within a predetermined range (e.g., approximately −100 to +300 V) may be applied to secondary electrons 20 and secondary electrons 20 may be attracted to a Faraday cage surrounding detector 150.

In addition, a predetermined voltage (e.g., approximately +12,000 V) may be applied to detector 150. In this case, as secondary electrons 20 approach detector 150, a strong attraction between secondary electrons 20 and detector 150 may result in collisions strong enough to allow the secondary electrons 20 to pass a thin aluminum layer formed on detector 150. After passing through the aluminum layer, the secondary electrons 20 may collide with phosphorescent scintillator materials, thereby emitting scintilla. The emitted scintilla may fall incident onto a photomultiplier, which amplifies and converts the scintilla into a strong electric signal.

The image acquisition unit 160 is connected to the detector 150, and may convert the voltage signal amplified in detector 150 into image information corresponding to an inspected region of substrate 131. The image information may include grayscale levels of pixels corresponding to the inspected region. In one embodiment, the image acquisition unit 160 may function as an analog-digital (AD) converter for converting an analog voltage signal into digital image information.

The image processing unit 170 may compare the image information with reference image information for detecting defects in the inspected region of substrate 131. In one embodiment, image processing unit 170 may detect defects in the inspected region by comparing grayscale levels of pixels of a reference image with grayscale levels of pixels of the detected image. Defects may be detected based on this comparison. The display unit 180 may display the defects detected from the image processing unit 170.

The intensity of electron beam 10 incident on the surface of substrate 131 may be referred to as (or correspond to) an incident current or a probe current Ip. The probe current Ip may be measured from the Faraday cage as a sum of back-scattered electrons, the secondary electrons, and the absorbed electrons. For example, the intensity of electron beam 10 (that is, the magnitude of the probe current Ip) can be measured by detector 150. The probe current Ip may be one factor for determining the quality and resolution of an image. Additional factors for determining the intensity of probe current Ip may include a drawing voltage and a heating current applied to the filament of the electron beam source 110 and the electron gun. That is, in one embodiment, the intensity of probe current Ip may be adjusted by adjusting the drawing voltage and heating current.

Figure 2:
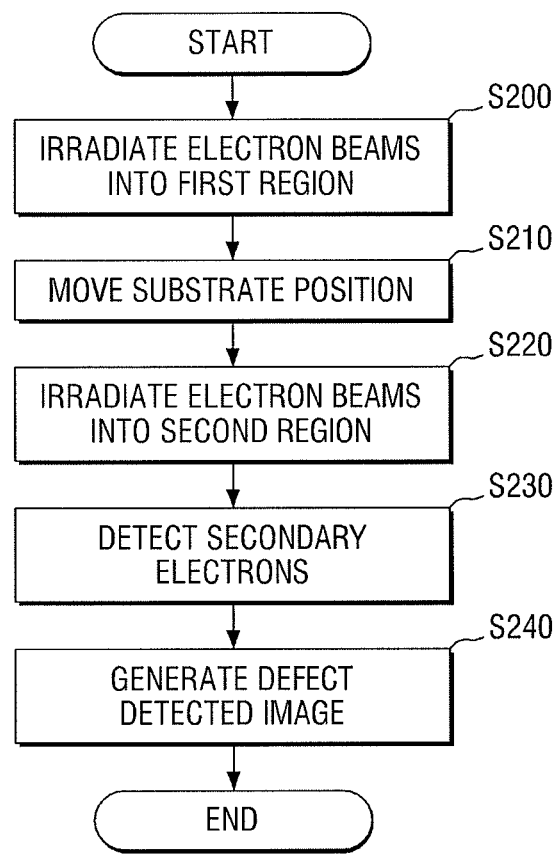
FIG. 2 illustrates an embodiment of a method for detecting a substrate defect.
Figure 3:
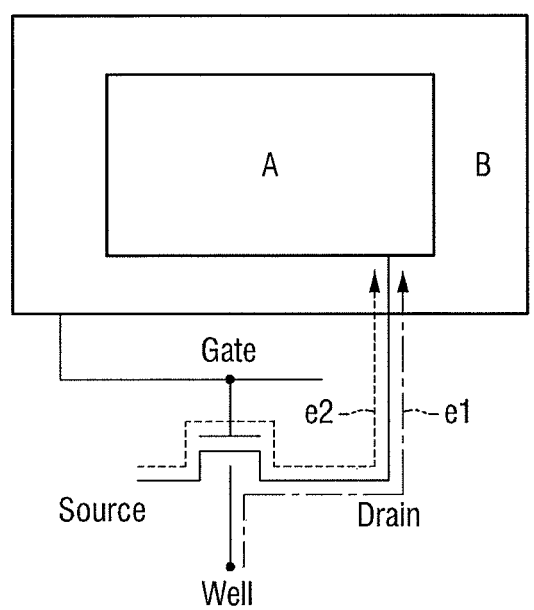
FIG. 3 illustrates an exemplary region of a substrate.
Figure 4:
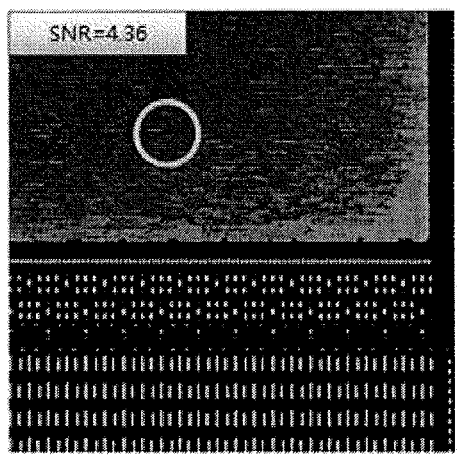
FIG. 4 illustrates an image of a detected defect generated from one type of device.
Figure 5:
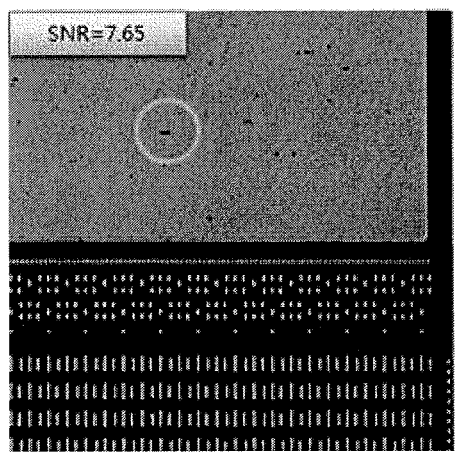
FIG. 5 illustrates an image of a detected defect acquired by one embodiment of a method for detecting a substrate defect.
Figure 6:
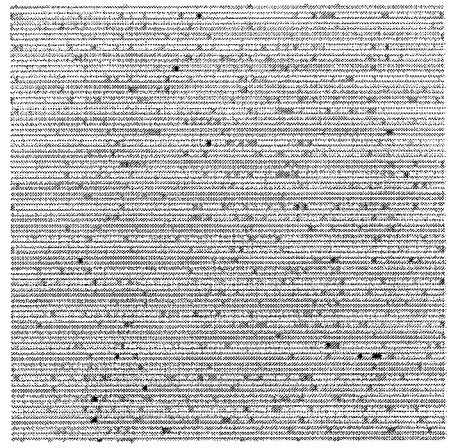
FIG. 6 illustrates an image acquired by a scanning electron microscope (SEM) using one type of method.
Figure 7:
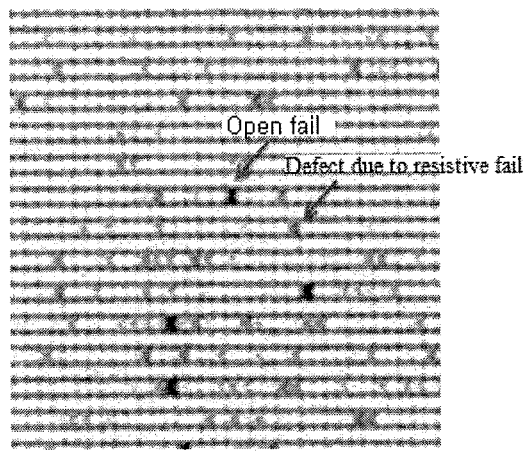
FIG. 7 illustrates an SEM image acquired by one embodiment of a method for detecting a substrate defect.
Figure 8:
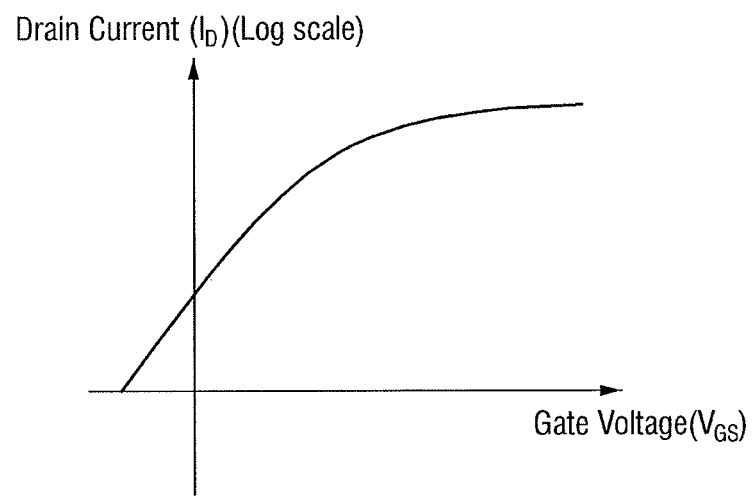
FIG. 8 illustrates a relationship between gate voltage and drain current.

FIG. 2 illustrates an embodiment of a method for detecting a defect of a substrate. FIG. 3 illustrates an exemplary region of a substrate. FIG. 4 illustrates a defect detected image acquired by one type of detecting method. FIG. 5 illustrates a defect detected image acquired by at least one method embodiment for detecting a substrate defect. FIG. 6 illustrates a scanning electron microscope (SEM) image acquired by the method of FIG. 4. FIG. 7 illustrates an SEM image acquired by at least one method embodiment for detecting a substrate defect. FIG. 8 is a graph illustrating a relationship between gate voltage and drain current.

Referring to FIG. 2, in one operation, electron beams 10 are irradiated into a first region B of a substrate (S200). The irradiating operation may be performed using, for example, the aforementioned substrate defect detecting apparatus. The first region B may be a region corresponding to a peripheral region of substrate 131. For example, the first region B may be a region different from an inspected region for detecting a defect of substrate 131 (e.g., first region B may include a gate region) and may serve as a current source. The electron beam 10 may be irradiated at a predetermined angle into a surface of first region B. For example, electron beam may be vertically irradiated into the surface of first region B. In this latter case, the intensity of the electron beam 10 reaching substrate 131 may be maximized.

In a subsequent operation, the position of substrate 131 is moved (S210). For example, consider the case where the substrate defect detecting apparatus includes a single electron beam source 110. In this case, the position of substrate 131 is moved in order to irradiate electron beam 10 from first region B to a second region A. Moving the position of substrate 131 may be performed by driver 140.

In a subsequent operation, electron beam 10 is irradiated into the second region A, which may be electrically connected to first region B (S220). The second region A may be a region corresponding to a cell region (or other predetermined region) of substrate 131. In one embodiment, second region A may be a target region in which a defect is to be inspected. For example, second region A may include may include a drain region.

As previously indicated, in irradiating electron beam 10 into second region A, electron beam 10 may be vertically irradiated (or radiated at another angle) into a surface of the second region A. In a case where electron beam 10 is vertically irradiated into the surface of substrate 131, the intensity of electron beam 10 reaching substrate 131 may be maximized.

The first region B and second region A may be adjacent to each other or may be separated from each other. Because first region B and second region A are electrically connected to each other, a detected amount of electrons emitted from second region A may be increased by irradiating electron beam 10 into first region B.

In a case where first region B and second region A are separated, in order to irradiate electron beam 10 into second region A, column 120 of the defect detecting apparatus may be moved to make the electron beam 10 reach second region A. That is, the irradiated position of electron beam 10 may be moved from first region B to second region A by moving substrate 131. However, if a distance between first region B and second region A is considerably large (or exceeds some predetermined distance), the irradiated position of electron beam 10 may also be moved from first region B to second region A by moving column 120. In one embodiment, the position of substrate 131 and column 120 may be moved.

In a subsequent operation, the secondary electrons 20 emitted from second region A are detected (S230). Detecting the secondary electrons 20 may be performed by detector 150.

In a subsequent operation, an image I is generated that includes defect. (S240). The image I may be generated based on detected amount of secondary electrons 20. That is to say, if a relatively large amount of secondary electrons 20 is detected, the secondary electrons 20 appear as relatively bright portions in the defect detected image I. If a relatively small amount of secondary electrons 20 is detected, the secondary electrons 20 appear as relatively dark portions in the defect detected image I. The relatively large and small amounts may be determined, for example, based on a predetermined reference value. In such a manner, it may be determined whether there is a defect in substrate 131. If there is a defect, a location of the defect in substrate 131 may be detected.

In one embodiment, the brightness of the relatively bright portions in the defect detected image I may further be increased. Since first region B and second region A are electrically connected to each other, a detected amount of electrons emitted from second region A can be increased by irradiating electron beam 10 into first region B, described with reference to FIG. 3. The second region A is a target region for inspection and first region B is a region different from the inspection target region and is electrically connected to second region A. Here, it is assumed that first region B is connected to a gate region and second region A is connected to a drain region.

Referring to FIG. 3, according to one embodiment, when electron beam 10 is irradiated into the first region B, a potential difference may be generated in the gate region. In addition, when electron beam 10 is irradiated into second region A, a potential difference may be generated between the source region and the drain region. As the result, electrons e2 may move from the source region to the drain region (see FIG. 8.). Therefore, when secondary electrons 20 emitted from the surface of second region A are detected, electrons e1 supplied from a well to second region A are supplied from the source region to the drain region. Electrons e1 are then added to electrons e2 supplied to second region A, thereby increasing the detected amount of the secondary electrons 20 emitted from the surface of second region A.

As described above, if the detected amount of secondary electrons 20 emitted from the surface of second region A is increased, a brightness difference between a defect-free portion of the defect detected image I and a portion of image I corresponding to a defect (e.g., an open fail or a resistive fail) is pronounced or maximized, thereby improving the SNR of the detecting apparatus while increasing its detection capability.

In accordance with one embodiment, it is possible to determine whether the SNR has improved or not. An example of how improvement in the SNR may be determined is shown by comparing FIGS. 4 and 5.

FIG. 4 illustrates a defect detected image I1 acquired by irradiating electron beam 10 only into second region A. FIG. 5 illustrates a defect detected image I2 acquired by irradiating electron beam 10 into second region A after irradiating electron beam 10 into first region B in accordance with an example embodiment. In FIGS. 4 and 5, a portion indicated by a circle indicates a defect due to an open fail. As shown in FIGS. 4 and 5, the SNR is improved by approximately 1.7 times from 4.36 to 7.65, and noise improvement effects can be demonstrated, to thereby allow the defect to be clearly detected.

Referring to FIGS. 6 and 7, a resistive fail may also be detected according to one or more embodiments. FIG. 6 illustrates an SEM image acquired by irradiating electron beam 10 only into second region A. FIG. 7 illustrates an SEM image acquired by irradiating electron beam 10 into second region A after irradiating the electron beam 10 into first region B in accordance with an example embodiment. In FIG. 7, dark portions may be easily distinguished from the background and/or other surrounding portions of the image. The darker portion corresponds to an open fail defect, as labeled in FIG. 7. The lighter (e.g., grayish) dark portion corresponds to a resistive fail defect. Referring to FIG. 6, a resistive fail defect may not be detectible when electron beam 10 is only irradiated into second region A.

Figure 9:
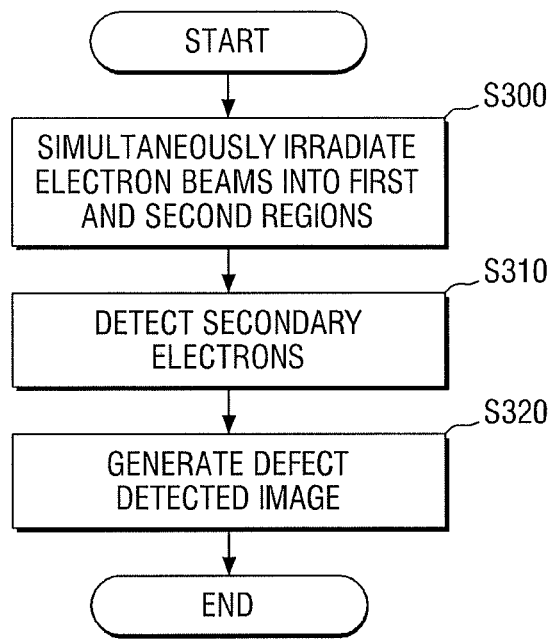
FIG. 9 illustrates another embodiment of a substrate defect detecting method.

FIG. 9 illustrates another embodiment of a method for detecting a defect of a substrate. For the sake of convenient explanation, the following description will focus on differences from the previous embodiments.

Referring to FIG. 9, first, electron beam 10 is simultaneously irradiated into a first region B of substrate 131 and a second region A electrically connected to the first region B (S300). The simultaneous irradiating of electron beam 10 into the first and second regions B and A may comprise irradiating electron beam 10 using first electron beams irradiated toward first region B and second electron beams irradiated toward the second region A.

In accordance with one embodiment, this may be accomplished using a defect detecting apparatus that includes a plurality of columns 120. With such an apparatus, electron beams 10 are simultaneously irradiated into first region B and second region A. Here, the first electron beam may be irradiated (vertically or at another angle) into a surface of first region B and the second electron beam may be irradiated (vertically or at another angle) into a surface of second region A. When the first electron beams and the second electron beams are vertically irradiated into the surface of the substrate 131, the intensity of the first and second electron beams on substrate 131 may be maximized.

In a subsequent operation, secondary electrons 20 emitted from second region A are detected (S310). Detecting secondary electrons 20 may be performed by detector 150.

In a subsequent operation, a defect detected image I is generated (S320). Generating the defect detected image I may include generating image I using a detected amount of secondary electrons 20. That is to say, if a relatively large amount of secondary electrons 20 is detected, the secondary electrons 20 are shown as relatively bright portions in the defect detected image I. If a relatively small amount of the secondary electrons 20 is detected, secondary electrons 20 are shown as relatively dark portions in the defect detected image I. In such a manner, it may be determined whether there is a defect in substrate 131. If image I contains a defect, the location of the defect in substrate 131 may be detected.

Figure 10:
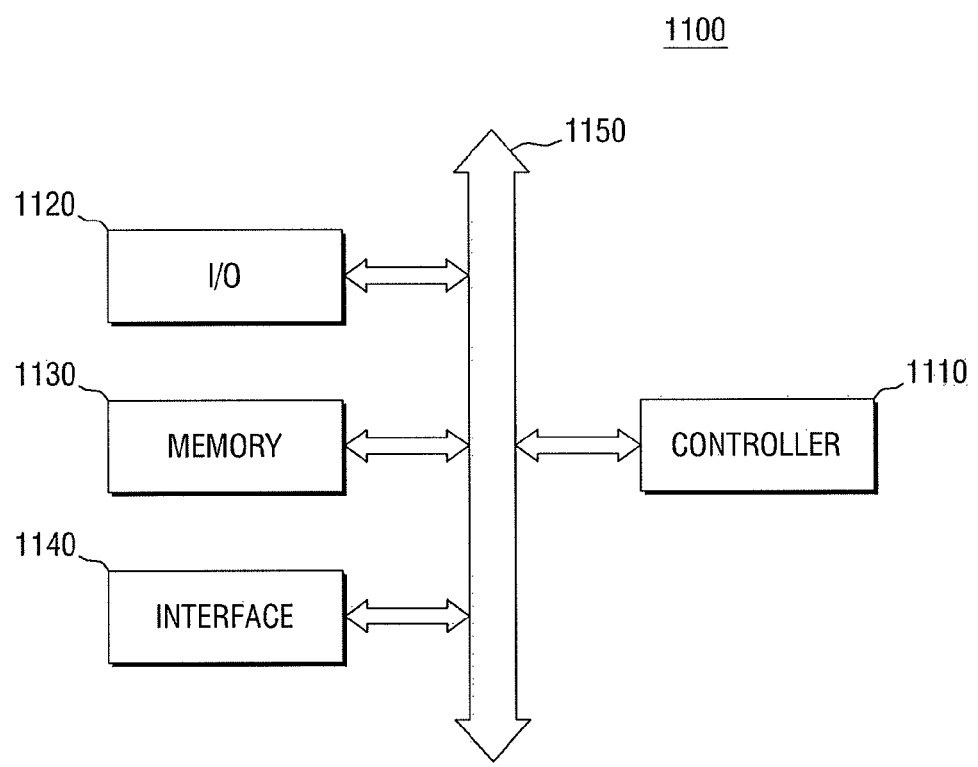
FIG. 10 illustrates an embodiment of an electronic system.

FIG. 10 illustrates an embodiment of an electronic system 1100 which includes a semiconductor device as previously mentioned. The electronic system 1100 includes a controller 1110, an input/output device (I/O) 1120, a memory device 1130, an interface 1140, and a bus 1150. The controller 1110, the I/O 1120, the memory device 1130, and/or the interface 1140 may be connected to each other through bus 1150. The bus 1150 corresponds to a path through which data moves.

The controller 1110 may include at least one of a microprocessor, a digital signal processor, a microcontroller, or logic elements capable of functions similar to those of these elements.

The I/O 1120 may include a key pad, a key board, a display device, and so on. The memory device 1130 may store data and/or codes. The interface 1140 may perform functions of transmitting data to a communication network or receiving data from the communication network. The interface 1140 may be wired or wireless. For example, the interface 1140 may include an antenna or a wired/wireless transceiver. The electronic system 1100 may further include high-speed DRAM and/or SRAM as an operating memory for improving operation of controller 1110.

The electronic system 1100 may be included in or correspond to a personal digital assistant (PDA), a portable computer, a web tablet, a wireless phone, a mobile phone, a digital music player, a memory card, or any type of electronic device capable of transmitting and/or receiving information in a wireless environment.

Figure 11:
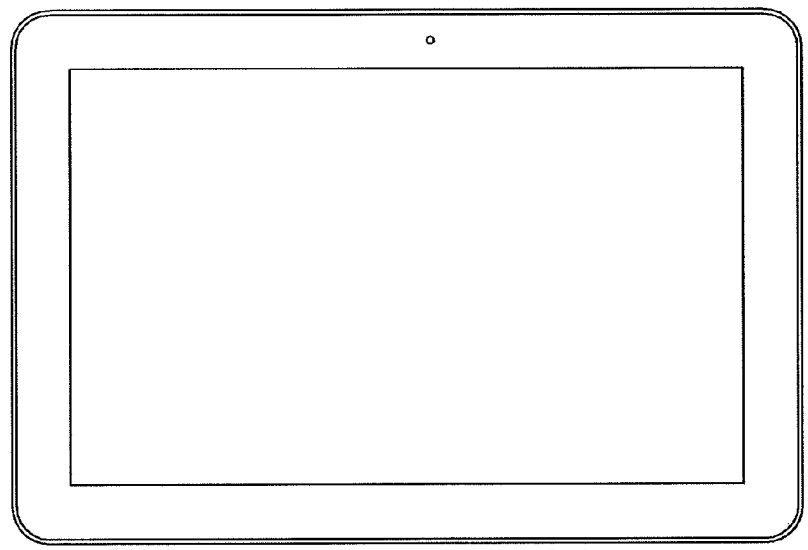
FIGS. 11 and 12 illustrate examples of semiconductor systems.
Figure 12:
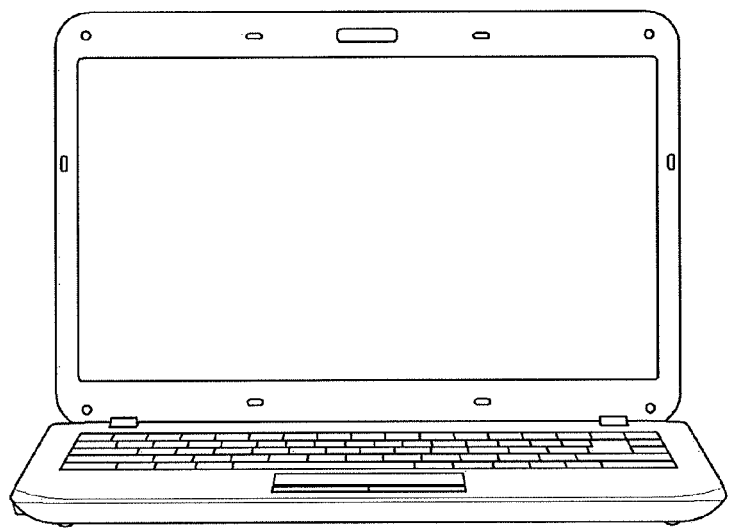

FIGS. 11 and 12 illustrate embodiments of a semiconductor system which may include a semiconductor device as previously discussed. FIG. 11 illustrates an example in which a semiconductor device is applied to a tablet PC, and FIG. 12 illustrates an example in which a semiconductor device is applied to a notebook computer. In other embodiments, the semiconductor device may be applied to other IC-based devices.

In accordance with one or more embodiments, a method for detecting a defect in the substrate of a semiconductor device has an improved signal-to-noise (SNR) ratio, which may increase detection capability. In one embodiment, an inspection method is performed using electron beams, and the detected amount of electrons emitted from a contact region to be inspected is increased. In these or other embodiments, the method includes performing a dummy scan process to detect an open fail and/or a resistive fail in a contact region. The dummy scan process may improve the SNR and enhance an SEM image.

Example embodiments have been disclosed herein, and although specific terms are employed, they are used and are to be interpreted in a generic and descriptive sense only and not for purpose of limitation. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise specifically indicated. Accordingly, it will be understood by those of skill in the art that various changes in form and details may be made without departing from the spirit and scope of the present invention as set forth in the following claims.

What is claimed is:

1. A method for detecting defects, the method comprising:
    irradiating an electron beam into a first region of a substrate;
    irradiating an electron beam into a second region electrically connected to the first region;
    wherein the first region is a peripheral region and the second region is a cell region of the substrate; and
    detecting secondary electrons emitted from the second region.

2. The method as claimed in claim 1, wherein the first region and the second region are separated from each other.

3. The method as claimed in claim 1, further comprising generating an image indicating a defect of the substrate.

4. The method as claimed in claim 3, wherein the generating the image includes generating the image based on a detected amount of secondary electrons.

5. The method as claimed in claim 3, further comprising:
    detecting the defect as corresponding to a location in the image that has a grayscale value different from an adjacent location in the image.

6. The method as claimed in claim 1, wherein irradiating of the electron beam into the first region comprises vertically irradiating the electron beam into a surface of the first region, and the irradiating the electron beam into the second region comprises vertically irradiating the electron beam into a surface of the second region.

7. The method as claimed in claim 1, wherein the first region includes a gate region and the second region includes a drain region.

8. The method as claimed in claim 1, wherein the electron beam irradiated into the first region is the electron beam irradiated into the second region.

9. A method for detecting defects, the method comprising:
    simultaneously irradiating electron beams into a first region of a substrate and a second region electrically connected to the first region;
    wherein the first region is a peripheral region and the second region is a cell region of the substrate; and
    detecting secondary electrons emitted from the second region.

10. The method as claimed in claim 9, wherein simultaneously irradiating the electron beams into the first and second regions include simultaneously irradiating a first electron beam toward the first region and a second electron beam toward the second region.

11. The method as claimed in claim 10, wherein the first electron beam is vertically irradiated into a surface of the first region, and the second electron beam is vertically irradiated into a surface of the second region.

12. The method as claimed in claim 9, wherein the first region and the second region are separated from each other.

13. The method as claimed in claim 9, further comprising generating an image indicating a defect of the substrate.

14. The method as claimed in claim 13, wherein generating the image includes generating the image based on a detected amount of secondary electrons.

15. The method as claimed in claim 13, further comprising:
    detecting the defect as corresponding to a location in the image that has a grayscale value different from an adjacent location in the image.

16. A method for detecting defects, the method comprising:
    scanning an electron beam from a first region to a second region of a substrate, the second region corresponding to an inspection region;
    detecting secondary electrons emitted from the second region;
    wherein the first region is a peripheral region and the second region is a cell region of the substrate; and
    detecting a defect in the second region of the substrate based on the secondary electrons emitted from the second region, wherein the first region is electrically connected to the second region.

17. The method as claimed in claim 16, further comprising:
    generating an image based on the secondary electrons,
    wherein the image includes a first location and a second location, and
    wherein the first location has a first grayscale value that exceeds a reference value and the second location has a second grayscale value less than the reference value, the second location detected as corresponding to the defect.

18. The method as claimed in claim 17, wherein the generating the image includes generating the image based on a detected amount of the secondary electrons.

19. The method as claimed in claim 17, wherein the second grayscale value is darker than the first grayscale value.

* * * * *